(12) United States Patent
Orenga

(10) Patent No.: US 6,649,365 B1
(45) Date of Patent: Nov. 18, 2003

(54) INDOLAMINE DERIVATIVES FOR DETECTING PEPTIDASE ACTIVITY IN CULTURE MEDIA

(75) Inventor: Sylvain Orenga, Neuville S/Ain (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/582,988

(22) PCT Filed: Jan. 28, 1999

(86) PCT No.: PCT/FR99/00166
§ 371 (c)(1),
(2), (4) Date: Sep. 7, 2000

(87) PCT Pub. No.: WO99/38995
PCT Pub. Date: Aug. 5, 1999

(30) Foreign Application Priority Data

Jan. 28, 1998 (FR) .............................. 98 00917

(51) Int. Cl.$^7$ ............................... C12Q 1/37
(52) U.S. Cl. ............... 435/24; 435/29; 435/33; 435/34
(58) Field of Search ............... 435/24, 29, 33, 435/34; 436/172

(56) References Cited

U.S. PATENT DOCUMENTS

| | | | |
|---|---|---|---|
| 4,717,658 A | * | 1/1988 | Michaels ................ 435/19 |
| 5,210,022 A | | 5/1993 | Roth et al. |
| 5,358,854 A | | 10/1994 | Ferguson |
| 6,046,016 A | * | 4/2000 | Orenga ................. 435/24 |
| 6,300,363 B1 | * | 10/2001 | Stevens et al. ............ 514/415 |

FOREIGN PATENT DOCUMENTS

| | | |
|---|---|---|
| EP | 0 224 830 A2 | 6/1987 |
| EP | 0 224 830 * | 6/1987 |
| FR | 2 457 323 A1 | 5/1979 |
| FR | 2 671 100 A1 | 7/1992 |
| FR | 2 684 110 A1 | 9/1993 |
| WO | WO 98/04735 | 2/1998 |

OTHER PUBLICATIONS

Pearson B. The Histochemical Demonstration of Leucine Aminopeptides by Means of a New Indolyl Compound. Lab Invest 12 pp. 712–720, 1963.*

Horii Z. Studies on the Syntheses of Oxytocics. Yakugaku Zasshi 81 pp. 636–639, 1961.*

Pearson et al.; "The Histochemical Demostration of Leucine AminopeptidASE by Means of New Indolyl Compound"; Lab Invest 12 (1963); pp. 712–720.

Yarborough et al.; Adv. in Organic Chemistry, Methods and Results, vol. 13, Interscience Publishers (1963), pp. 159 et seq.

* cited by examiner

Primary Examiner—Ralph Gitomer
(74) Attorney, Agent, or Firm—Oliff & Berridge, PLC

(57) ABSTRACT

Compounds of formula X—NH—R, in which X represents an optionally substituted indol-3-yl group and R represents the acyl residue of an amino acid or of a peptide, enabling the detection of peptidase activity in a micro-organism culture medium, including a gelled medium, by forming a stain or fluorescence in the medium.

21 Claims, No Drawings

US 6,649,365 B1

INDOLAMINE DERIVATIVES FOR DETECTING PEPTIDASE ACTIVITY IN CULTURE MEDIA

The present invention relates to the use of at least one compound based on an indolamine derivative for revealing an aminopeptidase or peptidase activity in a microorganism culture, as well as to a method and a culture medium for detecting such an enzymatic activity or for identifying microorganisms which express or do not express this activity.

"Aminopeptidase" is the term generally given to an enzyme which is capable of cleaving, by hydrolysis, the amide group formed between an acyl amino acid and a primary amine, and "peptidase" is the term given to an enzyme which is capable of cleaving, by hydrolysis, the amide group formed between the acyl residue of a peptide and a primary amine. In the present application, the term "peptidase" may refer to, depending on the cases, both a peptidase as defined above and an aminopeptidase.

The detection and identification of microorganisms are very important in particular in medicine, in the agrifoods industry or for monitoring the environment (for example controlling water). Microorganisms may be sought for their pathogenicity, as contamination indicators, or for monitoring manufacturing methods.

Techniques for detecting and identifying microorganisms are currently based on searching for characteristic nucleotide sequences, on searching for antigens or antibodies, on culturing in selective or nonselective medium, or on searching for metabolic and in particular enzymatic activities (for example osidase, esterase, peptidase, oxidase, etc. activities).

Usually, the methods for detecting and identifying microorganisms combine several of these techniques. Culturing is thus used to multiply and select the desired microorganisms. In order to simplify their detection, it has been proposed to reveal biochemical activities by introducing, directly into the culture medium, molecules which produce a coloration or a fluorescence. Such media are termed detection media. The biochemical activities sought can be revealed by diverse methods such as:

physicochemically modifying the medium: for example changing pH, revealed with the aid of a coloured or fluorescent indicator (methyl-umbelliferone), changing the redox potential, revealed with the aid of a coloured (tetrazolium salt) or fluorescent indicator, reacting a molecule produced by the microorganisms with a compound present in the medium, which leads to a coloration, or alternatively hydrolysing molecules which release a coloured or fluorescent compound (naphthol, coumarin).

The hydrolyses detected are generally the result of the reaction of an enzyme produced by the microorganism with a natural or synthetic enzymatic substrate. These enzymatic activities are for example those of the following enzymes: esterases (for example lipases, phosphatases), osidases ($\beta$-galactosidase, $\beta$-glucuronidase, N-acetylhexosaminidase), peptidases (alanine aminopeptidase, trypsinase, gelatinase), DNAses, decarboxylases, deaminases, ureases, tryptophanases, oxidases, catalases, etc.

It is known moreover that gelled media are particularly well suited to culturing and isolating microorganisms from a sample, as well as to detecting "target" microorganisms in a mixture of microorganisms. On these media, microorganisms form colonies which can be detected with the naked eye, and it is highly desirable that the products of the biochemical activities sought remain localized on their site of production. This in fact makes it possible to distinguish a colony from its neighbours if they do not express the same activities. Various methods can thus be used which detect, for example, changes in pH (FR-A-2,671,100), esterase activities (FR-2,457,323), osidase activities (FR-A-2,684, 110), etc. It is of course possible to use several of these methods together in order to detect several species or strains, and/or in order to increase the sensitivity and/or specificity of the detection.

Patents U.S. Pat. No. 5,210,022 and U.S. Pat. No. 5,358, 854 describe chromogenic substrates which are sensitive to the action of $\beta$-galactosidase. These 3-hydroxyindole-derived substrates are, for example, indolyl-$\beta$-D-galactosides, the indole nucleus of which can carry halogen substituents in positions 4, 5, 6 or 7.

Document EP-A-0,224,830 describes a method for detecting Gram-negative bacteria in a urine sample, in which a natural extract originating from certain species of crab is added to the sample, and then, after incubation, the sample is brought into contact with a support containing a peptide substrate which comprises a chromogenic leaving group. The natural extract used contains a proenzyme, and if the sample contains Gram-negative bacteria in sufficient number, the endotoxins of these bacteria activate the proenzyme into an enzyme which is capable of cleaving the peptide substrate with formation of a coloured product on the support.

There is currently no means available, which is suitable for gelled media, for detecting microorganism aminopeptidase and peptidase activities. Specifically, the enzymatic substrates used so far have the drawback of releasing coloured or fluorescent molecules which diffuse in the gelled media, or which are revealed only with U.V irradiation (in the case of naphthylamine or of aminocoumarin), or which require the addition of reagents (in the case of naphthylamine), or the coloration of which is of relatively poor contrast in the reaction media used in microbiology (in the case of nitroaniline).

In the present application, a term such as (amino acid)-BIA or (peptide)-BIA refers to a compound such as 3-acylamino-5-bromoindole, the acyl of which is that of said amino acid or said peptide.

It is known that L-leucine-aminopeptidase has been demonstrated in mammalian histological sections by means of an enzymatic substrate, 3-L-leucylamino-5-bromoindole, also termed L-leucine-3-(5-bromo-indolamine), known as L-Leu-BIA for short, which produces a coloured compound after hydrolysis; see Pearson et al., 1963, Lab. Invest., 12: 712. In 1967, Yarborough et al., J. Reticuloendoth. Soc., 4: 390 repeated the technique of Pearson et al. in similar applications (histological sections). They specify that adding a mixture of potassium ferri- or ferrocyanide or copper sulphate inhibits the reaction.

In 1975, Lojda and Havrankova, Histochemistry, 43: 355 proposed to improve the method using the substrate L-Leu-BIA by adding a mixture of tetrazolium salt and phenazine methosulphate, the coloured reaction observed being derived, in this case, from reduction of the tetrazolium salt to formazan.

Document WO 98/04735, which was published after the priority date from which the present application benefits, describes the use of a 5-bromoindolamine acylation derivative, the acyl being chosen from leucyl and alanyl residues, as a revealing agent for demonstrating, by formation of a coloured product, a peptidase activity in a microorganism culture.

In the course of the studies which lead to the present invention, an investigation was, carried out as to whether it was possible to use this enzymatic substrate for detecting microorganisms cultured, in particular, on gelled media. During preliminary tests, L-Leu-BIA or L-Pro-BIA was added to a medium currently used to search for osidases, which is described in Example 1 below. It was not possible to demonstrate a leucine-aminopeptidase or proline-aminopeptidase activity, whatever the microorganism cultured in this medium (in particular genera Escherichia, Klebsiella, Citrobacter, Pseudomonas, Enterococcus, Staphylococcus and Streptococcus). Addition of the reagents proposed by Lojda and Havrankova was reflected by a more or less total inhibition of the growth of the microorganisms without allowing the revelation of a peptidase activity with L-Leu-BIA or L-Pro-BIA.

Conversely, if 7-L-leucylamino-4-methylcoumarin (L-Leu-AMC) or 7-L-prolylamino-4-methylcoumarin (L-Pro-AMC) is added to the same medium from Example 1, a fluorescence (and thus a leucine-aminopeptidase or proline-aminopeptidase activity) is detected with some of these same microorganisms (see Example 1). Similarly, in this medium, with osidase substrates (5-bromo-4-chloro-3-indolyl-β-D-galactoside and 6-chloro-3-indolyl-β-D-glucuronide), the β-galactos-idase and β-glucuronidase activities of the microorganisms can be detected.

It was not possible to demonstrate a peptidase activity with L-Leu-BIA or L-Pro-BIA with the medium used in Example 2 below either.

It has now been discovered that the absence of results with the indolamine derivatives was not due to an incompatibility with the microorganisms or to an inhibition of their multiplication during culture, but was due essentially to medium conditions. It has in fact been discovered that it is possible to reveal the peptidase activity of microorganisms with indolamine derivatives by using other culture media. The reasons for which certain media can be used and others cannot are unknown. However, it is possible to determine and develop, by simple routine tests similar to those described in the experimental section below, the media and/or ingredients which are suitable or which are unsuitable. The invention thus firstly consisted, in particular, in investigating, and ensuring that it was possible to find, culture media in which the indolamine-derived peptidase substrates which are mentioned above can be used to reveal the corresponding enzymatic activities in a microorganism culture.

It was thus discovered in particular that a medium which can be used is as follows, containing:

| | |
|---|---|
| Yeast extract | 0.5 to 25 g/l |
| Gelatine peptone | 0.5 to 25 g/l |
| NaCl | 0 to 50 g/l |
| and optionally: | |
| pH regulator, quantity sufficient for pH = | 3 to 9 |
| and/or: | |
| Gelling agent | 5 to 35 g/l |

The gelling agent is a conventional gelling agent, for example agar.

The pH chosen is a pH which is suitable for the microorganism studied. In the case of a gelled medium, the pH is preferably from 5 to 9. The pH can be adjusted, for example, with hydrochloric acid or sodium carbonate.

If L-Pro-BIA, for example, is added to such a medium and inoculation with microorganisms is carried out, depending on whether the microorganisms do or do not express L-Proline-aminopeptidase activity, brown or colourless colonies are obtained.

Comparable results have been obtained with substrates such as 3-acylamino-indole in which the acyl is the acyl residue of an amino acid or of a peptide.

A subject of the invention is thus the use of at least one compound of formula (I):

in which X represents an optionally substituted indol-3-yl group and R represents the acyl residue of an amino acid or of a peptide, the amine group(s) present in R being optionally in protected form, as a tracer agent, said agent to be added to a microorganism culture medium and making it possible to reveal, by formation of a coloration or a fluorescence in said medium, either a peptidase activity in said culture medium, or the presence of a microorganism or of a group of microorganisms expressing such an activity in said medium, with the exception of the use of a compound of formula (I) for which X represents a 5-bromoindol-3-yl group and R represents a leucyl or alanyl residue. Of course, the use according to the invention also makes it possible, where appropriate, to observe the absence of the peptidase activity sought and/or the absence of the microorganism(s) sought.

The amino acid or the peptide in which R represents the acyl residue satisfies the formula RCOOH.

In the compounds of formula (I), the amine group(s) present in R, and in particular the N-terminal amine group, can be, if desired, in a form which is protected in particular with the aid of the temporary amine protecting groups conventionally used in peptide chemistry. The presence or absence of such protecting groups has no influence on the formation of a coloured or fluorescent product when the peptidase activity sought is present in the culture medium studied.

The indolyl group represented by X in formula (I) can comprise one or more substituents in one at least of positions 1, 4, 5, 6 and 7. Said substituents can be chosen in particular from halogen, lower alkyl, aryl, aralkyl, lower alkoxy and aralkoxy substituents. In the present application, the lower alkyl and lower alkoxy substituents, like the alkyl groups of the aralkyl and aralkoxy substituents, comprise in particular from 1 to 4 carbon atoms. The halogen substituents can be fluorine, chlorine, bromine and iodine, in particular chlorine and/or bromine. The aryl substituents are in particular phenyl groups optionally substituted for example with lower alkyl, halogen or lower alkoxy groups. The substituent optionally present in position 1 is in particular a lower alkyl substituent, for example methyl. Among the substituted indol-3-yl groups represented by X, mention may be made in particular of the 4-chloro-, 6-chloro-, 5-bromo-, 1-methyl-, 4-methyl-, 5-methyl-, 4,7-dimethyl-, 4,6-dichloro-, 6,7-dichloro-, 4-chloro-5-bromo-, 4,5,7-trichloro-, 4,6,7-trichloro-, 4-chloro-5-bromo-7-methyl-, 5-methoxy-, 5-benzyl-, 5-benzyloxy- and 5-phenylindole derivatives.

In formula (I), when the R group represents the acyl residue of an amino acid, it is for example an alanyl, prolyl, leucyl, pyroglutamyl or arginyl residue. When the R group represents the acyl residue of a peptide, this peptide may comprise up to 10 amino acid residues, in particular up to 5 amino acid residues, and in particular up to 3 amino acid residues. Among the peptides from which the R group is derived, mention will be made in particular of those in which the C-terminal amino acid residue is chosen from leucine, alanine, proline and arginine residues. By way of example of a peptide, mention may be made of alanyl-phenylalanyl-proline, which gives derivatives of formula (I) for which R represents Ala-Phe-Pro—.

The compounds of formula (I) are soluble in aqueous media. They can be prepared according to the usual methods used in peptide synthesis. An indolamine of formula X—$NH_2$, X being as defined above, can in particular be reacted with a derivative of an amino acid or of a peptide, said amino acid or said peptide satisfying the formula RH, R being as defined above. Said amino acid or peptide derivative is a derivative with an activated carboxyl group and (an) amine group(s) which is(are) protected with the aid of a usual primary amine function-protecting group. The activated carboxyl group is a carboxyl group derivative which facilitates amide formation by reaction with primary amines, for example a mixed anhydride group. It is known that a mixed anhydride can be obtained by reacting for example an acid with a lower alkyl chloroformiate.

The protecting groups and their use are well known; see for example R. A. Boissonas, Adv. in Organic Chemistry, Methods and Results, Vol. 3, Interscience Publishers, 1963, pp. 159 and subsequent pages. In the present case, any primary amine-protecting groups used in particular in peptide chemistry can be used, for example the N-Cbz (N-benzyloxycarbonyl) or N-Boc (N-butyloxycarbonyl), which are known to be temporary amine group-protecting groups, these groups then being able to be restored, if desired, by a simple acid hydrolysis. By reacting the indolamine of formula X—$NH_2$ with the derivative with an activated carboxyl group and a protected amine group, and then optionally deprotecting the amine group(s), the compound of formula (I) is obtained. The indolamine of formula X—$NH_2$ can itself be obtained in particular according to a method which is similar to that described by Madelung, Leibigs Annalen der Chemie, Vol. 405, pp. 58–95 (1914).

The invention also relates to a method for revealing a peptidase activity in a microorganism culture in which a tracer agent of formula (I) as defined above is added to the culture medium for said microorganisms, and in which the possible formation, in the culture medium, of a coloured compound is sought, it being understood that if a coloured compound has formed, the peptidase activity sought is present, and it is absent if there is no formation of a coloured product. In the method of the invention, a culture medium which is preselected for its ability to allow the transformation of a substrate of formula (I) into a coloured product when a corresponding peptidase activity is present is of course used. A medium such as that described above can in particular be used.

In the present application, "coloured product" is the term given to a product which has an intrinsic colour when it is lit in white light for example, or a product which emits a fluorescence when it is subjected to ultraviolet or visible light irradiation, and the word "coloration" refers to both the presence of a coloured product which has an intrinsic colour when it is lit in white light, and the presence of a product which emits a fluorescence under the influence of an irradiation of appropriate wavelength.

The step in which the possible formation of a coloured compound is sought is of course implemented, where appropriate, after a culture period such that the microorganisms sought have multiplied sufficiently for the peptidase activity sought to be detectable if it is present.

The invention also relates to a microorganism culture medium containing, besides the ingredients required for culturing microorganisms, at least one compound of formula (I) as defined above.

The compounds of formula (I) are added to the culture medium at a concentration which is sufficient for detecting the peptidase activity sought. For this ,;detection, the appearance of a coloration or, optionally, the appearance of a fluorescence under ultraviolet or visible light irradiation is sought, either with the naked eye or with the aid of suitable optical means. This sufficient concentration can be predetermined in each case by routine experiments. The culture medium can contain, for example, from 25 to 2000 mg/L of the compound of formula (I).

One of the advantages of the compounds of formula (I) is that the coloured products that they form in the presence of a peptidase activity do not diffuse in gelled culture media.

They can thus be used in gelled media. They can also, of course, be used in liquid media.

Moreover, the substrates of formula (I) do not inhibit microorganism multiplication in culture media. They can thus be used by adding them to the culture medium at any time, including, if desired, before the start of the culture, at the start of the culture, or at the end of the culture. In the case of a gelled medium, it is of course preferable to introduce the compound of formula (I) during the preparation of the culture medium, before gelling of said medium.

The invention relates to a method for detecting a microorganism or a group of microorganisms in a sample which contains them or which is likely to contain them. This method comprises the steps consisting in adding at least one compound of formula (I) as defined above to a culture medium containing the sample, in seeking the possible formation of a coloured or fluorescent product in said medium and in comparing, where appropriate, the coloration or fluorescence obtained with that obtained with an authentic sample of the microorganism or of the group of microorganisms sought. In such a method, the detection is of course based on the expression or absence of expression, by the microorganism or by the group of microorganisms sought, of the peptidase activity that the tracer agent of formula (I) used makes it possible to reveal.

According to a particular embodiment of the method for detecting microorganisms according to the invention, at least one other tracer agent for detecting, by formation of a coloured or fluorescent product, an enzymatic activity which may be the same as that which is revealed with the aid of the compounds of formula (I) as defined above, but which is generally an enzymatic activity which is different from that revealed with the aid of the compounds of formula (I), can also be added to the culture. It can be for example an esterase, osidase or peptidase activity. Further information can thus be obtained, which is linked with an absence of coloration (or of fluorescence) or linked with a coloration which is modified with respect to the coloration obtained with a single enzymatic substrate. The other tracer agent chosen will have properties which are different from those of the indolamine derivatives of formula (I): for example, another tracer agent which is capable of giving a reaction product having a colour which is different from the colour produced by the indolamine of formula (I) will be chosen. The other tracer agent (or second tracer agent) will thus make it possible to reveal, due to its intrinsic colour or due to its fluorescence, the presence of an enzymatic activity for which it is specific. If the peptidase activity which can be revealed by the indolamine derivatives of formula (I) is also present, a modified coloration will be obtained which is different from the coloration given by the compound of formula (I) when it is used alone, and also different from said intrinsic colour given by the second tracer agent. Examples of use of several substrates, as well as the information which can be derived therefrom, are given below in the experimental section. Of course, the results may vary with each species or strain of microorganism studied. Each case likely to be of interest should thus undergo prior studies according to routine experiments.

The derivatives which are used to reveal different enzymatic activities, and which can be used as other tracer agents, are known tracer agents or analogues thereof. They are in particular indoxyl, coumarin, resorufin, naphthol, naphthylamine, nitrophenol, nitroaniline, rhodamine, hydroxyquinoline, fluorescein, etc. derivatives.

Among these other tracer agents which can be used in combination with the indolamine derivatives, mention may be made in particular of 5-bromo-4-chloro-3-indolyl-β-D-glucuronide, 6-chloro-3-indolyl-β-D-glucoside, L-alanine-7-amino-4-methylcoumarin, 4-methylumbelliferyl-N-acetyl-β-D-galactosaminide, resorufin-β-D-galactoside, β-naphthyl sulphate, AS-BI β-D-galactoside naphthol, L-alanine β-naphthyl-amide, o-nitrophenol-β-D-galactoside, carboxybenzoyl-L-arginine-p-nitroanilide, rhodamine-110-bis(L-leucine amide), hydroxyquinoline-β-D-glucoside and fluorescein diacetate.

The characteristics and advantages of the invention are illustrated with the following examples.

EXAMPLE 1

| | |
|---|---|
| Meat peptone ① | 15 g/l |
| Casein peptone ② | 3 g/l |
| NaCl | 5 g/l |
| Tris buffer | 0.5 g/l |
| Na$_2$HPO$_4$ | 1 g/l |
| Sodium citrate | 1 g/l |
| Glucose | 1 g/l |
| Sodium pyruvate | 2 g/l |
| Aqar | 13 g/l |

①Sold by: D.I.F.C.O.
②Sold by: D.I.F.C.O.

L-Pro-BIA, or 7-L-prolylamino-4-methylcoumarin (L-Pro-AMC) is added to this medium at a concentration of 200 mg/l. The various media obtained, which are distributed in Petri dishes, are inoculated with microorganisms. The dishes were incubated at 37° C. for 48 hours. The colonies formed were examined visually in ambient light and under a UV lamp (wavelength=365 nm) after incubation for 24 and 48 hours. The colour or the presence of fluorescence was noted. The microorganisms studied were: *Pseudomonas aeruginosa* and *Candida albicans*.

After culturing for 24 or 48 hours, no coloration is observed in the cultures containing L-Pro-BIA, although these cultures contain an L-Pro-peptidase activity which can be revealed in the cultures containing L-Pro-AMC: in this case the emission of a fluorescence under UV irradiation is observed.

When L-Ala-BIA, L-Leu-BIA, L-alanine-7-amino-4-methylcoumarin (L-Ala-AMC) or L-leucine-7-amino-4-methylcoumarin (L-Leu-AMC) is added to the above medium at concentrations of 200 mg/L, no coloration is observed in the case of the bromoindolamine (BIA) derivatives after culturing for 24 or 48 hours.

Conversely, with the aminomethylcoumarin (AMC) derivatives, the presence of the L-alanine-aminopeptidase and L-leucine-aminopeptidase activities in the case of *Escherichia coli*, *Klebsiella Pneumoniae*, *Citrobacter freundii*, *P. aeruginosa*, *Streptococcus agalactiae*, *Enterococcus faecium* and *Streptococcus pyogenes*, and an absence of these activities with *Staphylococcus epidermidis*, was able to be revealed.

EXAMPLE 2

L-Pro-BIA or L-Pro-AMC is added, at the concentration of 400 mg/L, to a 0.1 M phosphate buffer, pH 7.3, at 25° C. The medium obtained is distributed into the wells of microtitration plates which are inoculated with suspensions of *P. aeruginosa* or of *C. albicans*. The plates are incubated for 24 hours at 37° C. The wells are examined visually in ambient light and under a UV lamp, after incubation for 24 to 48 hours.

No coloration was noted with L-Pro-BIA, even though it is possible to reveal an L-Pro-aminopeptidase activity in wells in which L-Pro-BIA has been replaced with L-Pro-AMC.

Similarly, the addition of L-Leu-BIA to the abovementioned phosphate buffer did not make it possible to detect an L-leucine-aminopeptidase activity in the *E. coli*, *K. pneumoniae*, *C. freundii*, *P. aeruginosa*, *S. agalactiae*, *E. faecium* and *S. pyogenes* cultures, whereas this activity is detected, by emission of fluorescence after 24 to 48 hours, for these same bacteria, in the same buffer with L-Leu-AMC.

EXAMPLE 3

| | |
|---|---|
| Yeast extract ① | 6 g/l |
| Gelatin peptone ② | 5 g/l |
| NaCl | 8 g/l |
| Na$_2$CO$_3$ | 0.1 g/l |
| Agar | 13 g/l |

①Sold by BioMerieux
②Bio-Gelytone sold by BioMerieux

L-Pro-BIA, pyroglutamyl-BIA (Pyr-BIA) or Ala-Phe-Pro-BIA is added to this medium. These various media, which are distributed into Petri dishes, are inoculated with various microorganisms: *E. coli*, *K. pneumoniae*, *C. freundii*, *p. aeruginosa*, *S. agalactiae*, *E. faecium*, *S. pyogenes*, *S. epidermidis*, *C. albicans* and *C. tropicalis*. The dishes are incubated at 37° C. for 48 hours, and the colonies formed are examined visually after incubation for 24 and 48 hours. The colour was noted. The results are presented in Table 1 below:

TABLE 1

| Strains | | L-Pro-BIA | Pyr-BIA | Ala-Phe-Pro-BIA |
|---|---|---|---|---|
| *E. coli* | 24 H | —[1] | — | Brown[2] |
| Gram − | 48 H | — | — | Brown |
| *K. pneumoniae* | 24 H | — | — | Brown |
| Gram − | 48 H | — | Brown | Brown |
| *C. freundii* | 24 H | — | — | Brown |
| Gram − | 48 H | — | Brown | Brown |
| *P. aeruginosa* | 24 H | Brown | Brown | Brown |
| Gram − | 48 H | Brown | Brown | Brown |
| *S. agalactiae* | 24 H | NT[3] | — | Brown |
| Gram + | 48 H | NT | — | Brown |
| *E. faecium* | 24 H | NT | Brown | — |
| Gram + | 48 H | NT | Brown | — |
| *S. pyogenes* | 24 H | NT | Brown | Brown |
| Grain + | 48 H | NT | Brown | Brown |
| *S. epidermidis* | 24 H | NT | — | NT |
| Gram + | 48 H | NT | — | NT |
| *C. albicans* | 24 H | Brown | NT | NT |
| | 48 H | Brown | NT | NT |
| *C. tropicalis* | 24 H | — | NT | NT |
| | 48 H | — | NT | NT |

[1]Absence of coloration
[2]Brown = Colony colour
[3]NT = Not tested

In the medium used for this example, it is thus possible to reveal L-proline-aminopeptidase, pyro-glutamyl-aminopeptidase and alanine-phenylalanine-proline-peptidase activities with L-Pro-BIA, Pyr-BIA and Ala-Phe-Pro-BIA, respectively. The bacteria of the species E. faecium (colourless colonies with Ala-Phe-Pro-BIA) can in particular be distinguished from the bacteria of the genus Streptococcus studied (brown coloration with Ala-Phe-Pro-BIA). The species P. aeruginosa (brown colonies with L-Pro-BIA) can also be distinguished from the other Gram-negative bacteria studied. The yeast strains of the species C. albicans (brown colonies with L-Pro-BIA) can also be distinguished from those of the species C. tropicalis.

Identical results were obtained with a similar liquid medium, without agar.

EXAMPLE 4

L-Pro-BIA or Pyr-BIA, alone or in combination with 5-bromo-4-chloro-3-indolyl-β-D-glucoside (X-Glu), 6-chloro-3-indolyl-β-D-glucoside (Z-Glu) or 4-methyl-umbelliferyl-β-D-glucoside (MUGl), was incorporated in the medium of Example 3. These various media, which are distributed in Petri dishes, are inoculated with microorganisms. The dishes were incubated at 37° C. for 48 hours, and the colonies formed were examined visually in ambient light and under a UV lamp (wavelength=365 nm). The colours of the colonies obtained after incubation for 24 and 48 hours are presented in Table 2:

E. faecium and S. pyogenes, the S. agalactiae strains giving colourless colonies and those of the other two species giving coloured colonies. After incubation for 24 hours, it is also possible to distinguish the By bacteria E. faecium from the other bacteria studied due to their characteristic colour (variable depending on the medium).

What is claimed is:

1. A method for determining the presence or absence of a peptidase activity, comprising:

adding, as a tracer agent, at least one compound of formula (I):

X—NH—R  (I)

in which X represents an optionally substituted indol-3-yl group and R represents the acyl residue of an amino acid or of a peptide, the amine group(s) present in R being optionally in protected form, to a culture medium, and detecting formation of a coloured or fluorescent product in said culture medium;

wherein said tracer agent reveals the presence of either a peptidase activity in a microorganism culture, or the presence of a microorganism or of a group of microorganisms expressing such an activity in said medium, by formation of a coloration or a fluorescence in said medium, and wherein said tracer agent is not a compound of formula (I) for which X represents a 5-bromoindol-3-yl group and R represents a leucyl or alanyl residue.

TABLE 2

|  |  | L-Pro-BIA | | | | Pyr-BIA | | | |
| --- | --- | --- | --- | --- | --- | --- | --- | --- | --- |
| Strains | T** | 1 | X-Glu 2 | Z-Glu 3 | MUGL 4 | 5 | X-Glu 6 | Z-Glu 7 | MUGL 8 |
| E. coli | 24 H | — | — | — | — | — | — | — | — |
| Gram − | 48 H | — | — | — | — | — | — | — | — |
| K. pneumoniae | 24 H | — | Blue | Pink | Fluo | — | Blue | Pink | Fluo |
| Gram − | 48 H | — | Blue | Pink | Fluo | Brown | Blue – grey | Grey – pink | Brown + fluo |
| C. freundii | 24 H | — | Blue | Pink | Fluo | — | Blue | Pink | Fluo |
| Gram − | 48 H | — | Blue | Pink | Fluo | Brown | Blue – grey | Grey – pink | Brown + fluo |
| P. aeruginosa | 24 H | Brown | Brown | Brown | Brown | Brown | Brown | Brown | Brown |
| Gram − | 48 H | Brown | Brown | Brown | Brown | Brown | Brown | Brown | Brown |
| S. agalactiae | 24 H | NT | NT | NT | NT | — | — | — | — |
| Gram + | 48 H | NT | NT | NT | NT | — | — | — | — |
| E. faecium | 24 H | NT | NT | NT | NT | Brown | Blue – grey | Grey – pink | Brown + fluo |
| Gram + | 48 H | NT | NT | NT | NT | Brown | Blue – grey | Grey – pink | Brown + fluo |
| S. pyogenes | 24 H | NT | NT | NT | NT | Brown | Brown | Brown | Brown |
| Gram + | 48 H | NT | NT | NT | NT | Brown | Brown | Brown | Brown |
| C. albicans | 24 H | Brown | Brown | Brown | Brown | NT | NT | NT | NT |
|  | 48 H | Brown | Brown | Brown | Brown | NT | NT | NT | NT |
| C. tropicalis | 24 H | — | — | Pink | Fluo | NT | NT | NT | NT |
|  | 48 H | — | Blue | Pink | Fluo | NT | NT | NT | NT |

N* Medium No.
T** Culture time
— Absence of coloration
NT Not tested.

On media 2, 3 and 4, after incubation for 24 hours, it is possible to distinguish E. coli (absence of coloration) and P. aeruginosa (brown coloration) from the other Gram-negative bacteria. On these media, it is also possible to distinguish C. albicans from C. tropicalis, the two species producing colonies of different colours. Media 6, 7 and 8 allow the distinction between S. agalactiae and the species 2. Method according to claim 1, in which R represents the acyl residue of an amino acid or the acyl residue of a peptide comprising up to 10 amino acid residues.

3. Method according to claim 2, in which said peptide comprises up to 5 amino acid residues.

4. Method according to claim 2, in which R represents the acyl residue of the peptide Ala-Phe-Pro—.

5. Method according to claim 2, in which the C-terminal amino acid residue of said peptide is a leucine, alanine, proline or arginine residue.

6. Method according to claim 2, in which said peptide comprises up to 3 amino acid residues.

7. Method according to claim 1, in which R represents an alanyl, prolyl, leucyl, pyroglutamyl or arginyl residue.

8. Method according to claim 1, in which X represents an indol-3-yl group substituted in at least one of positions 1, 4, 5, 6 and 7 of said indole group.

9. Method according to claim 8, in which X represents a 5-bromoindol-3-yl group.

10. Method according to claim 1, in which said culture medium is a gelled medium.

11. Method according to claim 1, in which said culture medium is a liquid medium.

12. Method according to claim 1, in which at least one other tracer agent for detecting, by formation of a coloured or fluorescent product, an enzymatic activity is also added to the culture medium.

13. Method according to claim 12, in which said other tracer agent makes it possible to detect an enzymatic activity which is different from that revealed with the aid of the tracer agent of formula (I).

14. A method for revealing a peptidase activity in a microorganism culture medium comprising the steps of:

adding to the culture medium at least one compound of formula (I):

  (I)

in which X represents an optionally substituted indol-3-yl group and R represents the acyl residue of an amino acid or of a peptide, the amine group(s) present in R being optionally in by protected form, with the exception of a compound of formula (I) for which X represents a 5-bromoindol-3-yl group and R represents a leucyl or alanyl residue, detecting the formation of a coloured or fluorescent product in said medium, and correlating the formation or absence of formation of a coloured or fluorescent product with the presence or absence of said peptidase activity, respectively.

15. Method according to claim 14 in which R represents the acyl residue of an amino acid or the acyl residue of a peptide comprising up to 10 amino acid residues.

16. Method according to claim 14, in which said compound of formula (I) is added to the culture medium before the start of a culturing step or at the start of a culturing step for said microorganism or for said group of microorganisms which are likely to be present in said sample.

17. Method according to claim 16, in which said culture medium is a gelled medium, and in which the compound of formula (I) is introduced during the preparation of the culture medium, before gelling of said medium.

18. Method for detecting a microorganism or a group of microorganisms in a sample which contains said microorganism or said group of microorganisms or which is likely to contain said microorganism or said group of microorganisms, comprising the steps of:

adding to the culture medium at least one compound of formula (I):

  (I)

in which X represents an optionally substituted indol-3-yl group and R represents the acyl residue of an amino acid or of a peptide, the amine group(s) present in R being optionally in protected form, with the exception of a compound of formula (I) for which X represents a 5-bromoindol-3-yl group and R represents a leucyl or alanyl residue, detecting the formation of a coloured or fluorescent product in said culture medium, and comparing, where appropriate, the coloration or fluorescence obtained with that obtained with an authentic sample of the microorganism or of the group of microorganisms sought.

19. Method according to claim 18 in which R represents the acyl residue of an amino acid or the acyl residue of a peptide comprising up to 10 amino acid residues.

20. Method according to claim 18 in which said compound of formula (I) is added to the culture medium before the start of a culturing step or at the start of a culturing step for said microorganism or for said group of microorganisms which are likely to be present in said sample.

21. Method according to claim 20, in which said culture medium is a gelled medium, and in which the compound of formula (I) is introduced during the preparation of the culture medium, before gelling of said medium.

* * * * *